US012678494B2

(12) United States Patent (10) Patent No.: US 12,678,494 B2
Jo et al. (45) Date of Patent: Jul. 14, 2026

(54) **IMMUNOGENIC COMPOSITION COMPRISING MULTIVALENT *STREPTOCOCCUS PNEUMONIAE* POLYSACCHARIDE-PROTEIN CONJUGATES**

(71) Applicant: CELLTRION INC., Incheon (KR)

(72) Inventors: Kyung Min Jo, Incheon (KR); Pan Kyeom Kim, Incheon (KR); Wan Geun La, Incheon (KR); Soo Young Lee, Incheon (KR); Jun Won Chwa, Incheon (KR); Ji Hyoun Cha, Incheon (KR)

(73) Assignee: CELLTRION, INC., Incheon (KR)

( * ) Notice: Subject to any disclaimer, the term of this patent is extended or adjusted under 35 U.S.C. 154(b) by 342 days.

(21) Appl. No.: 18/271,946

(22) PCT Filed: Jan. 13, 2022

(86) PCT No.: PCT/KR2022/000646
§ 371 (c)(1),
(2) Date: Jul. 12, 2023

(87) PCT Pub. No.: WO2022/154520
PCT Pub. Date: Jul. 21, 2022

(65) Prior Publication Data
US 2024/0066110 A1 Feb. 29, 2024

(30) Foreign Application Priority Data

Jan. 14, 2021 (KR) ........................ 10-2021-0005339

(51) Int. Cl.
*A61K 39/09* (2006.01)
*A61K 39/00* (2006.01)
*A61K 39/116* (2006.01)
*A61P 37/04* (2006.01)

(52) U.S. Cl.
CPC ............ *A61K 39/092* (2013.01); *A61K 39/00* (2013.01); *A61K 39/116* (2013.01); *A61P 37/04* (2018.01); *A61K 2039/55505* (2013.01); *A61K 2039/6037* (2013.01); *A61K 2039/70* (2013.01)

(58) Field of Classification Search
CPC .................................................. A61K 39/092
See application file for complete search history.

(56) References Cited

U.S. PATENT DOCUMENTS

| | | | |
|---|---|---|---|
| 10,300,135 B2 | 5/2019 | Porro | |
| 11,013,799 B2 | 5/2021 | Li | |
| 2005/0214329 A1* | 9/2005 | Laferriere ............ | A61K 39/092 424/244.1 |
| 2012/0301502 A1 | 11/2012 | Caulfield et al. | |
| 2019/0224295 A1 | 7/2019 | Matur et al. | |
| 2020/0197503 A1 | 6/2020 | Abeygunawardana et al. | |
| 2020/0237889 A1 | 7/2020 | An et al. | |
| 2021/0154287 A1 | 5/2021 | Kim et al. | |

FOREIGN PATENT DOCUMENTS

| | | |
|---|---|---|
| JP | 2019-529497 | 10/2019 |
| KR | 10-2017-0016360 | 2/2017 |
| KR | 10-2018-0105590 | 9/2018 |
| KR | 10-2019-0055063 | 5/2019 |
| KR | 10-2020-0005458 | 1/2020 |
| WO | WO 2019-203599 | 10/2019 |
| WO | WO 2021/010798 | 1/2021 |
| WO | PCT/KR2022/000646 | 5/2022 |

* cited by examiner

*Primary Examiner* — Albert M Navarro
(74) *Attorney, Agent, or Firm* — Wells St. John P.S.

(57) ABSTRACT

The present invention relates to an immunogenic composition including multivalent pneumococcal polysaccharide-protein conjugates. Each conjugate includes capsular polysaccharides of different pneumococcus serotypes conjugated to a carrier protein. More concretely, the present invention is a multivalent immunogenic composition including polysaccharide-protein conjugates. Each of the polysaccharide-protein conjugates includes *Streptococcus pneumoniae*-derived capsular polysaccharides of different serotypes conjugated to a carrier protein. The capsular polysaccharides include a) capsular polysaccharides of one or more serotypes selected from the group consisting of serotypes 1, 3, 4, 5, 6A, 6B, 7F, 9V, 14, 18C, 19A, 19F, and 23F, and b) capsular polysaccharides of one or more serotypes selected from the group consisting of serotypes 10A, 11A, 12F, 15B, 22F, 23A, and 35B. The multivalent immunogenic composition according to the present invention is capable of inducing an immune reaction against a wider variety of serotypes than the conventional Prevenar 13. In particular, the conventional Prevenar 13 is designed mainly for serotypes frequently appearing in Europe and North America, but the immunogenic composition of the present invention is an immunogenic composition having high coverage not only in Europe and North America but also throughout Asia. Therefore, the multivalent immunogenic composition according to the present invention is capable of being beneficially used to prevent diseases caused by pneumococcus in infants, children, and adults.

10 Claims, 4 Drawing Sheets

FIG. 1

IMMUNOGENIC COMPOSITION COMPRISING MULTIVALENT *STREPTOCOCCUS PNEUMONIAE* POLYSACCHARIDE-PROTEIN CONJUGATES

RELATED PATENT DATA

This application is filed under 35 U.S.C. § 371 and claims priority to PCT International Application No. PCT/KR2022/000646, filed 13 Jan. 2022, which claims priority to KR Application No. 10-2021-0005339, filed 14 Jan. 2021, each of which is incorporated herein by reference.

TECHNICAL FIELD

The present invention relates to an immunogenic composition including different multivalent pneumococcal polysaccharide-protein conjugates, each conjugate including pneumococcus-derived capsular polysaccharides of different serotypes conjugated to a carrier protein.

BACKGROUND ART

*Streptococcus pneumoniae* (hereinafter: pneumococcus) is an organism that is a major cause of pneumonia. According to a Statistics Korea report entitled "Death Rate Trends for Major Causes of Death in 2010," the death rate from pneumonia was 14.9 deaths per 100,000 people, making pneumonia one of the top 10 causes of death, and the death rate increased by 82.9% compared to 2000. According to a report of the World Health Organization (WHO) in 2012, 476,000 HIV-negative children under the age of five died from infection with pneumococcus in 2008, and 5% of all deaths worldwide in children under 5 years of age were attributable to diseases caused by pneumococcus in 2008.

In order to prevent diseases caused by pneumococcus, the world's first polysaccharide vaccine was developed by Harold J. White in 1931. However, since penicillin was developed in 1929, microbial infection diseases have been treated using antibiotics, but this results in the occurrence of antibiotic-resistant strains. Accordingly, treatment with conventional antibiotics becomes ineffective, so 6-valent polysaccharide vaccines were developed by Marie M. Dr Lapi of France in 1947. In 1977, 14-valent polysaccharide vaccines were developed by Dr. Robert Austrian and 17-valent polysaccharide vaccines were developed by Merck, Wyeth, and Pasteur, and the vaccines began to be sold worldwide. Then, 23-valent polysaccharide vaccines were developed. Multivalent pneumococcal polysaccharide vaccines have been proven to be useful in preventing pneumococcus diseases in elderly and high-risk patients. However, an immune reaction to most pneumococcal polysaccharides does not occur in infants and children, which is because of the T-cell independent immune reaction phenomenon. This phenomenon appears similarly in the case of other microbial vaccines. In order to overcome this phenomenon, a meningitis vaccine (Hib), which was the first polysaccharide-protein conjugation vaccine, was developed in 1987. Subsequently, technology for conjugation of vaccines of microorganisms such as those causative of meningitides, pneumococcus, and typhoid has been introduced. In the case of the pneumococcus conjugation vaccine, before a 7-valent pneumococcus conjugation vaccine was released in the United States in 2000, Pfizer (Wyeth), a developer, started developing a divalent pneumococcus conjugation vaccine in 1994 and developed a 7-valent type in 2000. The 7-valent pneumococcus conjugate vaccine (Prevenar®) includes capsular polysaccharides derived from the seven serotypes with the highest frequency of occurrence, namely 4, 6B, 9V, 14, 18C, 19F, and 23F. Since the vaccine was first approved in the United States in 2000, the vaccine has been demonstrated to be highly immunogenic and effective against invasive diseases and otitis media in infants and children. This vaccine is currently approved in about 80 countries worldwide. According to survey data accumulated over the years after the introduction of Prevenar, as expected, the incidence of invasive pneumococcus diseases caused by the serotypes included in Prevenar in the United States was clearly reduced. However, in some regions, the serotype coverage was limited, and the incidence of invasive pneumococcus diseases caused by serotypes not included in Prevenar increased. Subsequent to the 7-valent serotype, Pfizer selected six major serotypes causing invasive pulmonary diseases, and released the 13-valent pneumococcus conjugation vaccine (Prevenar 13) in 2010. Since then, it has been reported that serotype replacement occurs, in which the serotypes not included in the vaccine are prevalent, as in the case of the conventional 7-valent pneumococcus conjugation vaccine.

As the incidence of pneumococcus infections caused by serotypes not included in Prevenar 13 increased, studies on the addition of pneumococcus serotypes have continued. However, multivalent injections and combination with conjugates may result in competition (immunity interference effects) between different constituent components, and may adversely affect the immunogenicity of individual conjugates. Accordingly, adding conjugates to immunogenic compositions has been very difficult.

The immunity interference effect is a major issue in the development of multivalent vaccines, and has been raised as the major issue mainly during the development of pneumococcus vaccines. Since the introduction of PCV7 in 2000, the immunity interference effect in the pneumococcus vaccine significantly emerged when PCV10 was introduced in 2010. The vaccine was scheduled to be released as a PCV11-valent type, but Pn6B did not produce an immune reaction due to the immunity interference effect, so the vaccine was released as a PCV10 type except for 6B. Further, recently, from the results of phase 2 of clinical trials of PCV15, being developed by Merck (HUMAN VACCINES & IMMUNOTHERAPEUTICS, 2019, A dose ranging study of 2 different formulations of 15-valent pneumococcal conjugate vaccine (PCV15) in healthy infants), it has been confirmed that some serotypes exhibit immunogenicity lower than that of the positive control PCV13. In the current trend of developing pneumococcus vaccines in the form of multivalent vaccines, a multivalent vaccine composition that does not exhibit an immunity interference effect while securing immunogenicity of individual serotypes is essential for vaccine development.

This immunity interference phenomenon may limit the number of conjugates that may be included in the multivalent vaccine. Therefore, although protection against numerous serotypes is of considerable value, it is very difficult to achieve when the number of conjugates in the composition is limited.

Accordingly, the present inventors, based on the results of surveying serotypes that are prevalent in countries in the continent of Asia (Korea, China, Japan, Taiwan, Singapore, Australia, and India), finally selected serotypes 10A, 11A, 12F, 15B, 22F, 23A, and 35B as the serotypes that are prevalent in Asian countries. Also, the present inventors developed a PCV20 form by adding the corresponding seven types to conventional PCV13, thereby finally confirming that the combination of the corresponding immunogenic compositions does not cause an immunity interference effect.

This means that the final complementary measures to the serotypes that could not be covered by the conventional Prevenar 13 product significantly reduce the IPD prevalence rate in countries where PCV13 is not introduced, countries where NIP is not introduced, and countries where serotype replacement occurs.

DISCLOSURE

Technical Problem

Accordingly, the present inventors identified an immunogenic composition combination that is capable of covering serotypes not covered by the conventional Prevenar 13 product without immunity interference, thereby having completed the present invention.

Therefore, an objective of the present invention is to provide a multivalent immunogenic composition including polysaccharide-protein conjugates. Each of the conjugates includes capsular polysaccharides derived from *Streptococcus pneumoniae* of different serotypes conjugated to a carrier protein, and the capsular polysaccharides are 14- to 20-valent serotypes.

Another objective of the present invention is to provide a pharmaceutical composition for inducing an immune response against a *Streptococcus pneumoniae*-capsular polysaccharide conjugate, the pharmaceutical composition including an immunologically effective amount of the multivalent immunogenic composition.

A further objective of the present invention is to provide a method of preventing or treating pneumococcus-related diseases, the method including administering the multivalent immunogenic composition in a prophylactically or therapeutically effective amount.

A yet further objective of the present invention is to provide a prophylactic or therapeutic use of the multivalent immunogenic composition for pneumococcus-related diseases. The use includes administering the multivalent immunogenic composition in a prophylactically or therapeutically effective amount.

Technical Solution

In order to accomplish one objective of the present invention, there is provided a multivalent immunogenic composition including polysaccharide-protein conjugates. Each of the polysaccharide-protein conjugates includes *Streptococcus pneumoniae*-derived capsular polysaccharides of different serotypes conjugated to a carrier protein. The capsular polysaccharides include a) capsular polysaccharides of one or more serotypes selected from the group consisting of serotypes 1, 3, 4, 5, 6A, 6B, 7F, 9V, 14, 18C, 19A, 19F, and 23F, and b) capsular polysaccharides of one or more serotypes selected from the group consisting of serotypes 10A, 11A, 12F, 15B, 22F, 23A, and 35B.

In the multivalent immunogenic composition according to the present invention, the a) capsular polysaccharides may be 13 serotypes consisting of serotypes 1, 3, 4, 5, 6A, 6B, 7F, 9V, 14, 18C, 19A, 19F, and 23F, but are not limited thereto.

In the multivalent immunogenic composition according to the present invention, the carrier protein may be any one selected from the group consisting of a diphtheria toxoid, a tetanus toxoid, a whooping cough toxoid, a cholera toxoid, an *E. coli*-derived inactivated toxin, a *Pseudomonas aeruginosa*-derived inactivated toxin, and a bacterial outer membrane protein (OMP), but is not limited thereto.

In the multivalent immunogenic composition according to the present invention, the diphtheria toxoid may be any one selected from the group consisting of $CRM_{197}$, $CRM_{173}$, $CRM_{228}$, and $CRM_{45}$, but is not limited thereto. According to one embodiment of the present invention, the carrier protein may be $CRM_{197}$.

In the multivalent immunogenic composition according to the present invention, a method of conjugating the capsular polysaccharides to the carrier protein may be any one selected from the group consisting of a CDAP conjugation method, a reductive amination method, and a thiol-malemide method, but is not limited thereto.

The multivalent immunogenic composition according to the present invention may further include an adjuvant. For example, the multivalent immunogenic composition may include an aluminum salt as the adjuvant. The aluminum salt may be selected from the group consisting of aluminum phosphate, aluminum sulfate, and aluminum hydroxide, and preferably may be aluminum phosphate.

In order to achieve another objective of the present invention, there is provided a pharmaceutical composition for inducing an immune reaction against a *Streptococcus pneumoniae*-capsular polysaccharide conjugate. The pharmaceutical composition includes an immunologically effective amount of a multivalent immunogenic composition.

In one embodiment, the pharmaceutical composition may be an immunogenic composition formulated so as to include 2 μg of each saccharide (4 μg in the case of 6B), about 34 μg of a $CR_{197}$ carrier protein, 0.125 mg of an adjuvant of an aluminum element (0.5 mg of aluminum phosphate), and sodium chloride and a sodium succinate buffer solution as excipients, but is not limited thereto.

In order to accomplish a further objective of the present invention, there is provided a method of preventing or treating pneumococcus-related diseases. The method includes administering the above-described multivalent immunogenic composition in a prophylactically or therapeutically effective amount.

Moreover, in order to accomplish a yet further objective of the present invention, there is provided a prophylactic or therapeutic use of the multivalent immunogenic composition for pneumococcus-related diseases. The prophylactic or therapeutic use includes administering the above-described multivalent immunogenic composition in a prophylactically or therapeutically effective amount.

Advantageous Effects

The multivalent immunogenic composition according to the present invention is capable of inducing an immune reaction against a wider variety of serotypes than the conventional Prevenar 13. In particular, the conventional Prevenar 13 is designed and produced mainly for serotypes frequently appearing in Europe and North America, but the immunogenic composition of the present invention is an immunogenic composition having high coverage not only in Europe and North America but also throughout Asia. Therefore, the multivalent immunogenic composition according to the present invention is capable of being beneficially used to prevent diseases caused by pneumococcus in infants, children, and adults.

DESCRIPTION OF DRAWINGS

FIG. 1 is a view showing the IgG ELISA result of a 13-valent pneumococcus vaccine serotype;

BEST MODE

Figure 2:
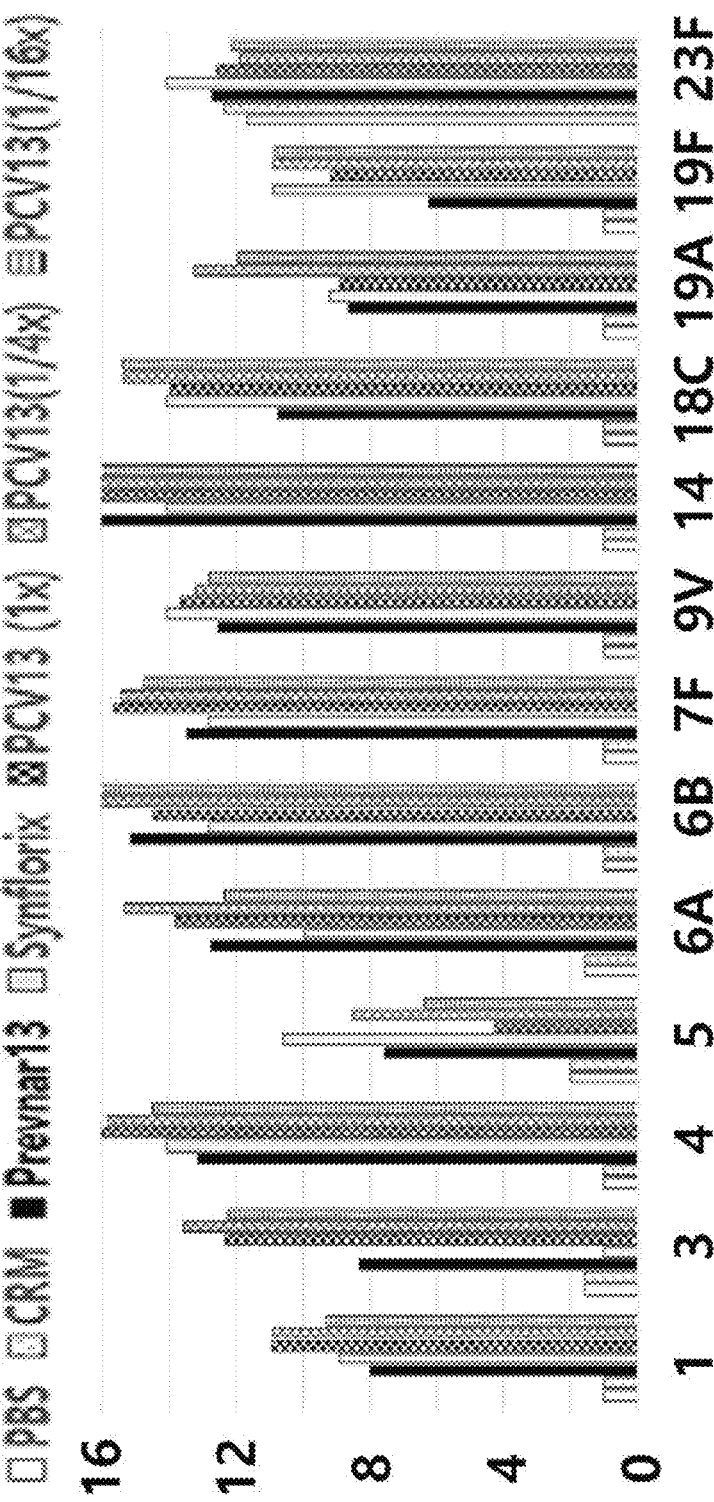
FIG. 2 is a view showing the OPA result of a 13-valent pneumococcus vaccine serotype.

Hereinafter, the present invention will be described in detail.

However, this description is only to aid the understanding of the present invention, and in any sense, the scope of the present invention is not limited by the details described in the detailed description of the invention.

Due to regional variation in serotype distribution, there is a limitation in that Prevenar coverage varies depending on the region. Therefore, there is no reason to remove any serotype from the conventional pneumococcus conjugate vaccine, but rather there is a need to broaden the coverage by adding serotypes.

The serotype of Prevenar 13 has been developed as the serotype that is prevalent in Europe and the United States, and a serotype replacement phenomenon occurred in each country after the introduction of Prevenar 13. A difference between Asia and Europe/USA has been reported. In the present invention, the serotypes that are prevalent in Asia and Europe/USA after the introduction of Prevenar 13 were selected. With respect to the standards of the prevalence rate of pneumococcus in each country, 1) children under 5 years of age, 2) prevalence rate results after the introduction of Prevenar 13 in each country, and 3) serotypes that are observed to be prevalent and not prevalent in each country were selected. The serotypes that are prevalent in all of Asia, Europe, and the United States are selected.

Serotype replacement is known to be affected by age, country, vaccine introduction time, or whether a national vaccine program (NIP, national immunization program) is introduced. Accordingly, in order to overcome this phenomenon, a pneumococcus vaccine developer is developing a new vaccine with a strategy to add representative serotypes causing IPD (invasive pulmonary diseases). Merck PCV15 is being developed in the form in which 22F and 33F are added to PCV13, and Pfizer PCV20 is being developed in the form in which 8, 10A, 11A, 12F, 15B, 22F, and 33F are added to PCV13. With respect to the criteria for selection of serotypes by Merck and Pfizer, prevalent serotypes that cause IPD in the United States and Europe were selected, and in particular, Merck selected 22F and 33F, which are serotypes common to the United States and Europe.

In the case of Japan, which is evaluated as an advanced country from the aspect of vaccination, PCV7 and PCV13 were registered in NIP of Japan immediately after release. In the case of the serotypes included in PCV13, after registration, a phenomenon in which the number of IPD patients was rapidly reduced was observed. This phenomenon occurs in common in the United States and Europe. However, the tendencies of occurrence of IPD of serotypes included in PCV13 are similar to each other, but it can be confirmed that serotypes prevalent in Non-PCV13 (serotypes not containing a vaccine) are different in terms of prevalence for each country/continent (Source 1. Vaccine 34 (2016) 67-76; Source 2. Vaccines 4 (2016), 2000-2014: A Pooled Data Analysis; Source 3. Plos one (2017) (A systematic review and meta-analysis).

In Japan, PCV7 and PCV13 were introduced in 2010 and 2013, respectively, and it is known that there is a large difference in prevalent serotypes before and after the introduction of the PCV13 vaccine. In the period from 2011 to 2013, which was the initial stage of PCV13 introduction, the incidence of PCV13-containing sera was frequent. However, a serotype replacement phenomenon occurred rapidly from 2014 to 2016, two to three years after the introduction of the vaccine. Among the serotypes contained in PCV13, the order of prevalence of recently prevalent serotypes was 3, 6A, 6B, 19F, 23F, but the number of patients is on the order of $\frac{1}{10}$ of the number before the vaccine was introduced. Since the introduction of the vaccine, non-PCV13 serotypes are prevalent and occur in the order of 24F>15A>12F>15B>22F.

For example, in the case of the United States, unlike the case of Japan above, 22F and 33F have been prevalent since the introduction of PCV13, but 33F is not greatly prevalent in the continent of Asia, including Japan (Source 1. Clin Microbiol Infect 2016; 22: 60.e9-60.e29, Source 2. WHO 2011, Global review of the distribution of pneumococcal disease by age and region, and Source 3. CDC (US) homepage).

Further, the time of vaccine introduction and the time of NIP introduction are different in the case of Europe. However, referring to the cases of UK/Germany/France, the order of prevalence of serotypes after the introduction of PCV13 is 8>22F>33F>24>9N, which is different from that in the continent of Asia (Expert review of vaccines. 2019).

The cases of Korea, Japan, Taiwan, China, Australia, Singapore, and India were investigated in order to confirm prevalent serotypes in the continent of Asia. People under the age of 5 years and over the age of 65 years were set as the basis of the investigation, and IPD epidemic serotypes after the introduction of PCV13 were confirmed. As a result, in the case of Japan, PCV13 was introduced in 2013, and the order of prevalence of Non-PCV13 serotypes was confirmed to be 24F>15A>12F>15B>22F. In the case of Korea, the order of prevalence of serotypes was confirmed to be 10A>15A, 23A>15B, 35B. In the case of Australia, the order of prevalence of serotypes was confirmed to be 23B>22F>35B>33F, and in the case of Taiwan, the order of prevalence of serotypes was confirmed to be 23A>15B>15A>22F, 11A. In the case of Singapore, there are few cases, but the prevalent Non-PCV13 serotypes were reported to be 15B and 15A. In the case of China/India, in both countries, the introduction time of NIP was late, and the results of epidemiological investigations were not obtained after the introduction of NIP (after 2017), so the serotypes that were prevalent were not produced. However, referring to serotypes that are prevalent in the countries noted above, there is a high possibility of occurrence of serotype replacement in both China and India, and it is expected that serotypes different from the serotypes prevalent in Europe and the United States and the same as the serotypes prevalent in Asia are highly likely to be prevalent.

As a result of analyzing serotypes that are prevalent in Asian countries, among the serotypes that are prevalent in Asia, the overlapping serotypes in three countries or more are 15B, 15A, 22F, and 23A, of which 15B and 15A are reported to exhibit cross-reactivity. Accordingly, a single serotype, 15B, was selected. Further, a total of seven types (10A, 11A, 12F, 15B, 22F, 23A, and 35B) were selected, including 35B, which is specific to Asian countries and 10A, 11A, and 12F, which are prevalent in Europe/USA including Asia.

In the case of Korea, Prevenar 13 was introduced in 2010, and serotype replacement occurred soon thereafter, as in Japan. Since 2016 to 2017, the prevalence of non-Prevenar 13 has increased. Among Prevenar 13 serotypes, the serotypes that have been prevalent until recently are 19F and 6A, and in the case of these serotypes, the number of patients and the frequency of outbreaks were significantly reduced compared to before the vaccine was introduced. Among non-Prevenar 13 types, the order of prevalence of serotypes after the introduction of the vaccine is 10A>15A, 23A>15B, 35B>12F.

In the case of Australia, Prevenar 13 was introduced in 2011. Since 2014, serotype replacement has been observed, and the incidence of non-Prevenar 13 serotypes has increased. Among non-Prevenar 13, the order of prevalence of serotypes since the introduction of the vaccine is 23B>22F>35B>33F.

In the case of Taiwan, Prevenar 13 was introduced in 2010. Since 2016, a serotype replacement phenomenon has been shown. Among non-PV13, the order of prevalence of serotypes since the introduction of the vaccine is 23A>15B>15A>22F, 11A, 12F.

In the case of Singapore, Prevenar 13 was introduced in 2011. As in other Asian countries, serotype replacement occurred after the introduction of the vaccine. Among non-Prevenar 13, the order of prevalence of serotypes is 15B>15A.

In the case of India, Prevenar 13 was introduced in 2017. Since only 1 to 2 years have passed since the introduction of Prevenar 13 in India, serotype replacement has not completely progressed. It is expected that serotype replacement will increase with increasing vaccine use. According to currently reported data, the order of prevalence of serotypes among non-Prevenar 13 types is 23A>22F>15B>6D.

In the case of China, Prevenar 7 and Prevenar 13 were approved for sale in 2008 and in 2016, respectively, but these were not included in the national free vaccination project, so the inoculation rate and distribution rate thereof are reported to be significantly low. However, the distribution rate of vaccines is increased as expectations for health increase according to China's economic growth, so a serotype replacement phenomenon is expected to occur with a time lag compared to the case of other countries.

As a result of listing the frequency of occurrence of non-Prevenar 13 serotypes after the introduction of Prevenar 13 in six Asian countries (Korea, Japan, Taiwan, Singapore, India, and Australia), 15B was confirmed to be most prevalent in six Asian countries, and to be prevalent in the order of 22F, 23A, and 35B. The serotypes that are prevalent in common in the United States and Europe are 22F and 23F, and the next prevalent serotypes are reported to be 10A, 11A, and 12F. Accordingly, seven serotypes that were prevalent in Asia (10A, 11A, 12F, 15B, 22F, 23A, and 35B) were added, and five serotypes that were prevalent in Europe and the United States (10A, 11A, 12F, 22F, and 35B) were added, thus selecting a final serotype constitution.

Accordingly, based on the results of surveying of serotypes that are prevalent in countries in the continent of Asia (Korea, China, Japan, Taiwan, Singapore, Australia, and India), the present inventors filially selected 10A, 11A, 12F, 15B, 22F, 23A, and 35B as the serotypes that are prevalent in Asian countries, and developed a final PCV20 form in which the corresponding seven types were added to the conventional PCV13.

Because vaccination is a nationally supported industrial sector, it is important to check whether a vaccine is included in a national free vaccine program in view of a vaccination rate. The types of vaccines included in the vaccine program (NIP) and the targets of vaccination differ greatly depending on the economic level and the position of the health authorities of each country. Among them, a pneumococcus conjugation vaccine is one of vaccines included in expensive vaccines, and only a few countries in the world include this vaccine in the national free vaccine program. Japan operates a national free vaccine program similar to that of other advanced countries, showing a pneumococcus inoculation rate similar to those of the United States and Europe, and as a result, serotype replacement occurred at a time similar to that in Europe and the United States. Differences in serotype replacement between Asian countries may be attributed to differences between races. However, a common denominator of serotype replacement can be found, which is different from the non-Prevenar 13 serotype that is prevalent in Europe and the United States. Among the 22F and 33F serotypes that are prevalent in common in Europe and the United States, the 33F serotype was found only in Australia, among Asian countries in which serotype replacement occurs, but not in Korea, Japan, Taiwan, Singapore, or India. Unlike in Europe and the United States, 15A, 15B, 22F, and 23A serotypes are prevalent in Asian countries, showing differences from the serotypes that are prevalent in Europe and the United States.

A 20-valent pneumococcus conjugate composition including seven new serotypes (10A, 11A, 12F, 15B, 22F, 23A, and 35B) of the present invention serves to induce a functional immune reaction in humans against diseases caused by pneumococcus infection. More concretely, in an embodiment, a human subject is an elderly subject, and the disease is pneumonia or an invasive pneumococcus disease. More concretely, in an embodiment, the elderly subject is at least 50 years of age. More concretely, in an embodiment, the elderly subject is at least 55 years of age. More concretely, in an embodiment, the elderly subject is at least 60 years of age.

More concretely, in an embodiment, the human subject is an infant, and the disease is pneumonia, an invasive pneumococcus disease (IPD), or acute otitis media (AOM).

More concretely, in an embodiment, the infant refers to a baby of 0 to 2 years old or a baby of 2 to 15 months old.

In another embodiment, the human subject is in the age of 6 weeks to 17 years, and the disease is pneumonia, an invasive pneumococcus disease (IPD), or acute otitis media (AOM). In a specific embodiment, the human subject is in the age of 6 weeks to 5 years. In another embodiment, the human subject is in the age of 5 weeks to 17 years.

The present invention provides a multivalent immunogenic composition including a capsular polysaccharide-protein conjugate. The capsular polysaccharide-protein conjugate includes all serotypes in which Prevenar 13 is included in a vaccine, and further includes one or more serotypes selected from the group consisting of 10A, 11A, 12F, 15B, 22F, 23A, and 35B. That is, the present invention is a multivalent immunogenic composition including fourteen or more different polysaccharide-protein conjugates together with a physiologically acceptable vehicle. Each of the conjugates includes pneumococcus-derived capsular polysaccharides of different serotypes conjugated to a carrier protein.

The capsular polysaccharide may be manufactured using a standard technique known to those skilled in the art. The capsular polysaccharide may be reduced in size in order to reduce the viscosity or increase the solubility of the activated capsular polysaccharide. In an embodiment of the present invention, the capsular polysaccharide is manufactured as one or more serotypes of capsular polysaccharides selected from thirteen serotypes consisting of pneumococcus serotypes 1, 3, 4, 5, 6A, 6B, 7F, 9V, 14, 18C, 19A, 19F, and 23F and selected from the group consisting of serotypes 10A, 11A, 12F, 15B, 22F, 23A, and 35B.

These pneumococcal conjugates are manufactured using separate processes and formulated into a single-dosage form. For example, each pneumococcal polysaccharide serotype proliferates in a soybean-based medium, and then individual polysaccharides are purified using centrifugation, precipitation, and ultrafiltration.

The carrier protein is preferably a non-toxic, non-reactive protein that is obtainable in sufficient quantity so as to have sufficient purity. The carrier protein must be suitable for a standard conjugation method. In the multivalent immunogenic composition according to the present invention, the carrier protein may be $CRM_{197}$. $CRM_{197}$ is a non-toxic variant of a diphtheria toxin separated from cultures of *Corynebacterium diphtheria* strain C7 (13197) that proliferates in a casamino acid and yeast-extract-based medium. $CRM_{197}$ is purified using ultrafiltration, ammonium sulfate precipitation, and ion exchange chromatography. $CRM_{197}$ may be manufactured using genetic recombination according to U.S. Pat. No. 5,614,382.

Other diphtheria toxoids may also be used as the carrier protein. Examples of other suitable carrier proteins include a tetanus toxoid, a whooping cough toxoid, a cholera toxoid, and inactivated bacterial toxins such as *E. coli*- and *Pseudomonas aeruginosa*-derived exotoxin A. A bacterial outer membrane protein, for example, outer membrane complex c (OMPC), porin, transferrin-combined protein, pneumolysin, pneumococcus surface protein A (PspA), pneumococcus adhesin protein (PsaA), C5a peptidase derived from Group A or Group B streptococci, or *Haemophilus influenzae* protein D may also be used. Other proteins such as ovalbumin, keyhole limpet hemocyanin (KLH), bovine serum albumin (BSA), or purified protein derivatives (PPD) of tuberculin may also be used as the carrier protein. Diphtheria toxin variants such as $CRM_{173}$, $CRM_{228}$, and $CRM_{45}$ may also be used as the carrier protein.

In order to conjugate the carrier protein and the polysaccharide, a conventionally known conjugation method may be used. For example, a reductive amination method, a CDAP conjugation method, or a thiol-malemide method may be used, without limitation thereto. In order to manufacture saccharides that react with the carrier protein, the purified polysaccharide may be chemically activated. Once the polysaccharide is activated, the capsular polysaccharides are conjugated to the carrier protein one by one to form glycoconjugates. In an embodiment, each of the capsular polysaccharides is conjugated to the same carrier protein. Chemical activation of the polysaccharides and subsequent conjugation of the polysaccharides to the carrier protein may be performed using known methods (U.S. Pat. Nos. 4,673, 574 and 4,902,506).

The obtained polysaccharide-protein conjugate may be purified using various methods (that is, the amount of the polysaccharide-protein conjugate may be increased). Examples of these methods include concentration/dialysis filtration processes, column chromatography, and multilayer filtration. The purified polysaccharide-protein conjugates may be mixed with each other so as to be formulated into the immunogenic composition of the present invention, and this composition may be used as a vaccine. Formulation of the immunogenic composition of the present invention may be performed using a method recognized in the art. For example, each of fourteen to twenty pneumococcus conjugates may be formulated with a physiologically acceptable vehicle to manufacture a composition. Examples of the vehicle include water, buffered saline, polyols (e.g.; glycerol, propylene glycol, or liquid polyethylene glycol), and dextrose solutions, but are not limited thereto.

In an embodiment, the immunogenic composition of the present invention includes one or more adjuvants. An "adjuvant" as defined herein is a material used to increase the immunogenicity of the immunogenic composition of the present invention. Therefore, the adjuvant is often provided to boost an immune reaction, and is well known to those skilled in the art. The adjuvant suitable for increasing the effectiveness of the composition includes, but is not limited to, the following:

In a specific embodiment, an aluminum salt is used as the adjuvant. The aluminum salt adjuvant may be an aluminum-precipitated vaccine or an aluminum-adsorbed vaccine. Examples of the aluminum salt include hydrated alumina, alumina hydrates, and alumina trihydrates (ATH), but are not limited thereto. When aluminum chloride and sodium phosphate are mixed at a ratio of 1:1, aluminum hydroxyphosphate sulfate is precipitated. A high shear mixer is used to make the size of the precipitate 2 to 8 μm, and dialysis is performed using physiological saline, followed by sterilization, thus manufacturing the adjuvant. In an embodiment, commercially available $Al(OH)_3$ (for example, Alhydrogel or Superfos) is used to adsorb proteins. 50 to 200 g of proteins per mg of aluminum hydroxide may be adsorbed, and this ratio is dependent on the pI of the protein and the pH of the solvent. A protein having a low pI is bonded more strongly than a protein having a high pI. The aluminum salt forms an antigen reservoir that slowly releases an antigen for two to three weeks, which non-specifically activates macrophages, complements, and innate immune mechanisms.

The present invention provides a pharmaceutical composition (for example, a vaccine formulation) for inducing an immune reaction to a *Streptococcus pneumoniae*-capsular polysaccharide conjugate. The pharmaceutical composition includes an immunologically effective amount of the multivalent immunogenic composition.

The vaccine formulations according to the present invention may be administered through systemic or mucosal routes so as to protect or treat a person susceptible to pneumococcus. The "effective amount" as defined herein refers to a dose necessary to induce an antibody to an extent capable of significantly reducing the probability or severity of infection with pneumococcus. The administration may include intramuscular injection, intraperitoneal injection, intradermal injection, or subcutaneous injection; or mucosal administration to the oral/digestive tract, respiratory tract, or genitourinary tract. In an embodiment, intranasal administration is performed for the treatment of pneumonia or otitis media, and this is because nasopharyngeal pneumococcus can be more effectively prevented, thereby weakening the infection at an early stage.

The amount of the conjugate in each vaccine dose is selected as an amount sufficient to induce an immune protective reaction without significant side effects. This amount may vary depending on the serotype of pneumococcus. In general, each dose may include 0.1 to 100 μg, preferably 0.1 to 10 μg, and more preferably 1 to 5 μg of polysaccharide, without limitation thereto. The optimal amount of an ingredient for a specific vaccine may be confirmed by standard studies involving observation of a suitable immune reaction in a subject. For example, through the extrapolation of the results of animal experiments, the dose of vaccine inoculation in humans may be determined. Further, the dose may be empirically determined.

In an embodiment of the present invention, the vaccine composition of the present invention is a sterilized liquid formulation that includes capsular polysaccharides of thirteen serotypes consisting of serotypes 1, 3, 4, 5, 6A, 6B, 7F, 9V, 14, 18C, 19A, 19F, and 23F, each conjugated to $CRM_{197}$, and also includes capsular polysaccharides of one or more serotypes selected from the group consisting of serotypes 10A, 11A, 12F, 15B, 22F, 23A, and 35B. The composition may be formulated so as to include: 2 μg of each saccharide (4 μg in the case of 6B); about 34 μg of a $CRM_{197}$ carrier protein; 0.125 mg of an aluminum element as an adjuvant (0.5 mg of aluminum phosphate); and sodium chloride and a sodium succinate buffer solution as excipients, in 0.5 mL of the dose. The liquid may be charged in a single-dose syringe without a preservative. Immediately after being shaken, the liquid vaccine takes the form of a homogeneous white suspension that can be administered intramuscularly.

The composition of the present invention may be formulated in the form of single-administration dose vials, multi-administration dose vials, or pre-filled syringes.

The formulation of the present invention may include a surfactant, and the formulation may include a mixture of surfactants such as Tween 80 or Span 85.

In an embodiment of the present invention, the present invention provides a method of preventing or treating pneumococcus-related diseases. The method includes administering the above-described multivalent immunogenic composition in a prophylactically or therapeutically effective amount.

In an embodiment of the present invention, the present invention provides a prophylactic or therapeutic use of the above-described multivalent immunogenic composition for pneumococcus-related diseases. The prophylactic or therapeutic use includes administering the above-described multivalent immunogenic composition in a prophylactically or therapeutically effective amount.

Inclusion of Prevenar 13 Serotype

In Northern California, the Prevenar 13 serotype accounted for more than 90% of all cases of invasive pneumococcus diseases in infants and children. Further, in Western Europe, the Prevenar 13 serotype accounted for more than 70% of all cases of invasive pneumococcus diseases in infants and children Since the United States and Europe are the largest vaccine markets, there is no reason to remove any Prevenar 13 serotype from the next-generation pneumococcus conjugation vaccine, but rather it is preferable to add other serotypes, thus broadening the scope of application thereof.

Addition of 7-Valent Serotype

The serotype of Prevenar 13 was developed as a serotype that was prevalent in Europe and the United States, and a serotype replacement phenomenon has occurred in each country since the introduction of Prevenar 13, and has been reported to show a difference between Asia, Europe, and the United States. In the present invention, the serotypes that are prevalent in Asia and Europe/USA after the introduction of Prevenar 13 were selected. With respect to the standards of the prevalence rate of pneumococcus in each country, 1) children under 5 years of age, 2) prevalence rate results after the introduction of Prevenar 13 in each country, and 3) serotypes that are examined to be prevalent and not prevalent in each country are selected.

Herein after, the present invention will be described in greater detail through Examples. However, the following Examples are for the purpose of illustrating the present invention, and the present invention should not be construed as being limited by these Examples.

Example 1. Manufacture and Purification of Pneumococcal Capsular Polysaccharides Cultivation of pneumococcus and purification of capsular polysaccharides were performed using a method known to those skilled in the art Each pneumococcus serotype may be obtained from a designated agency (CDC, Center for Disease Control and Prevention). Pneumococcus was identified using non-motility with capsules, a gram-positive characteristic, lancet-shaped diplococcus, and an alpha hemolysis phenomenon in blood agar media. The serotype was confirmed based on a Quellung test using a specific antiserum.

Example 1-1. Manufacturing of Cell Bank

Twenty different Pneumococcus serotypes (1, 3, 4, 5, 6A, 6B, 7F, 9V, 10A, 11A, 12F, 14, 15B, 18C, 19A, 19F, 22F, 23A, 23F, and 35B) were obtained from the American Type Culture Collection (ATCC, US), which is a designated agency in the United States.

Pneumococcus strains were smeared on a blood agar medium to separate single colonies. After a single colony which was well grown was selected among ten or more single colonies, inoculation with the liquid medium that did not contain animal-derived components was performed, followed by cultivation, thus manufacturing a research cell bank (RCB) containing synthetic glycerol.

One vial was drawn from a research cell bank in which expression of the polysaccharide having a unique serotype was confirmed, and cells were proliferated in a liquid medium that did not contain animal-derived components. Synthetic glycerol was then added thereto to manufacture a master cell bank. One vial was drawn from the master cell bank, and cells were proliferated in a liquid medium that did not contain animal-derived components. Synthetic glycerol was then added thereto to manufacture a cell bank for manufacture. The manufactured cell bank was stored at −70° C. or below for use in the next step.

Example 1-2. Fermentation and Separation of Polysaccharides

One vial of a cell bank for manufacturing was thawed to perform inoculation with a liquid medium that did not contain animal-derived components, thereby initiating sub-fermentation. Sub-cultivation was performed at 37±2° C. in an unstirred state until a predetermined fungus concentration (optical density, OD600) was attained, indicating that the end point of the mid-exponential phase was reached. Inoculation with the culture medium obtained in the sub-cultivation was performed in a fermentation device containing a liquid medium that did not contain animal-derived components, thereby initiating main fermentation.

Next, cultivation was performed while adjusting the pH of the medium with a potassium hydroxide solution at 37±2° C. The optimal cell density and the concentration of glucose contained in the medium were measured every 2 hours. Fermentation was terminated when glucose in the medium was depleted.

After the fermentation was completed, 12% sodium deoxycholate was added to the culture for 1 hour until the final concentration was 0.12%, thus dissolving the cells and isolating the polysaccharides bonded to the cells.

Example 1-3. Purification of Capsular
Polysaccharide

After phosphoric acid was added to the sample treated with sodium deoxycholate, the supernatant was recovered through centrifugation. The recovered supernatant was passed through a depth filter, and then concentration and buffer exchange with a phosphate buffer solution were performed. After the buffer exchange, the sample was passed through an activated carbon filter, and impurities were then removed using the following two methods.

Since eighteen serotypes 1, 3, 4, 5, 6A, 6B, 9V, 10A, 11A, 12F, 15B, 18C, 19A, 19F, 22F, 23A, 23F, and 35B are capable of being ion-bonded to CTAB (cetyltrimethylammonium bromide), a CTAB process was performed. CTAB treatment, centrifugation, treatment with sodium chloride (NaCl) and sodium iodide (NaI), and centrifugation were performed.

An aluminum phosphate gel (Algel) solution was added to two serotypes 7F and 14 that did not react with CTAB, thereby performing the reaction. Then, the supernatant obtained through centrifugation was used.

The two types of samples subjected to an impurity removal process were subjected to depth filter and ultrafiltration (UF/DF) processes, and then converted into the form of original powders while the amounts of ethanol and sodium chloride were adjusted, followed by storage.

Example 1-4. Dissolution and Hydrolysis of
Capsular Polysaccharides

The capsular polysaccharide original powder derived from each of the serotypes was dissolved in water for injection so that the final concentration was within the range described below, and was filtered using a 0.45 μm filter.

In detail, serotypes 1, 3, and 4 were dissolved so that the concentration was in the range of 0.8 to 2.0 mg/ml, serotypes 5, 6B, 9V, 18C, and 19F were dissolved so that the concentration was in the range of 4 to 8 mg/ml, serotypes 6A and 19A were dissolved so that the concentration was in the range of 8 to 12 mg/ml, and serotypes 7F, 10A, 11A, 12F, and 23F were dissolved so that the concentration was in the range of 2 to 4 mg/ml, followed by filtration. Further, serotypes 15B, 22F, and 35B were dissolved so that the concentration was in the range of 2 to 5 mg/ml, followed by filtration.

The solution was subjected to constant-temperature treatment in the pH and temperature ranges described below for each serotype. Specifically, serotypes 1, 3, 5, 6B, 7F, 10A, 11A, 12F, 14, and 23F were subjected to the constant-temperature treatment process at 70° C. to 80° C. overnight, serotypes 6A and 19F were subjected to the constant-temperature treatment process at 70° C. to 80° C. for 1 to 4 hours, and serotypes 9V and 18C were subjected to the constant-temperature treatment process at 65° C. to 80° C. at a pH of 2.0 for 1 to 3 hours using a phosphoric acid solution. Serotypes 22F, 23A, and 35B were subjected to the constant-temperature treatment process at 75° C. to 85° C. overnight, and serotypes 4, 15B, and 19A were not hydrolyzed. Then, cooling was performed to the temperature range of 21° C. to 24° C. and sodium hydroxide was added until a target pH of 6.0±1.0 was obtained at which point hydrolysis was stopped.

Example 2. Conjugation and Purification of
Pneumococcal Capsular Polysaccharides and
CRM$_{197}$ Protein Carrier Example 2-1. Preparation of CRM$_{197}$ Protein
Carrier The host cell of the CRM$_{197}$ protein carrier, *Corynebacterium diphtheriae*, was obtained from the Institution of Accession, the American Type Culture Collection (ATCC, US) and produced based on known techniques. Briefly, an ammonia precipitation method and an anion exchange chromatography method were used to produce CRM$_{197}$ from a *C. Diptheriae* culture medium.

Example 2-2. Conjugation of Capsular
Polysaccharides to CRM$_{197}$

Sodium chloride powder was added to all serotypes to manufacture a 2 M NaCl polysaccharide solution. CDAP (1-cyano-4-dimethylaminopyridinium tetrafluoroborate) that was appropriate for each serum was dissolved at a ratio of 1 g of CDAP per 100 ml of a solution of 50/50 acetonitrile/water for injection (v/v). In detail, based on the polysaccharides, CDAP was dissolved at a weight ratio of 1 w/w % in the case of serotypes 6A and 14, CDAP was dissolved at a weight ratio of 2 w/w % in the case of serotype 4, and CDAP was dissolved at a weight ratio of 3 w/w % in the case of serotypes 1, 3, 6B, 7F, 15B, and 19A. CDAP was dissolved at a weight ratio of 4 w/w % in the case of the other serotypes, and they were added to each polysaccharide solution. Subsequently, after the sodium hydroxide solution was added so as to raise the pH to 9.4 to 9.7 after 1 to 3 minutes, stirring was performed for 3 to 7 minutes so that the hydroxyl group of the polysaccharides was sufficiently activated by CDAP. Based on the polysaccharides, 0.5 to 1.0 w/w % of CRM$_{197}$ was added to the polysaccharide solution for each serotype, thus performing a conjugation reaction for 1 to 4 hours. A reaction conversion ratio was measured using HPLC-SEC, and CDAP was further added as necessary.

Example 2-3. Termination of Conjugation Reaction 3 to 6 molar equivalents of glycine solution were added based on 1 molar equivalent of CDAP added for all serotypes, and the pH was adjusted to 9.0, thereby terminating the reaction. The conjugation solution was stirred at 21° C. to 24° C. for 1 hour and then stored at a low temperature of 2° C. to 8° C. overnight.

Example 2-4. Ultrafiltration

The diluted conjugation mixture was concentrated and dialyzed to be filtered using a filter for ultrafiltration using a minimum of 20 volumes of a buffer solution. The buffer solution was maintained at a pH in the range of 5.5 to 6.5, and a buffer solution containing 0.9% sodium chloride was used. As the filter for ultrafiltration, the filter for a fractional molecular weight of 300 kDa was used for all serotypes, and the permeation solution was discarded.

Example 2-5. Sterile Filtration

The residual liquid after filtration by dialysis was diluted using a buffer solution so that the concentration thereof was less than 0.4 g/L based on the concentration of the polysaccharides that were contained, and was then filtered using a 0.22 μm filter. The filtered product (the content of saccharides or residual DMAP thereof) was controlled during the manufacturing process. The filtered residual liquid was controlled during the manufacturing process, thus determining whether additional concentration, filtration by dialysis, and/or dilution was required.

Example 3. Formulation and Immunogenic Studies of 13-Valent Pneumococcus Vaccine

Example 3-1. Formulation of 13-Valent Pneumococcus Vaccine

The final volume of the final bulk concentrate obtained from Example 2 was calculated based on the batch volume and the concentration of bulk saccharides. 0.85% sodium chloride (physiological saline), polysorbate 80, and a succinate buffer solution were added to the pre-labeled formulation container, followed by addition of the bulk concentrate. Thereafter, the formulations were mixed thoroughly and subjected to sterile filtration using a 0.2 μm membrane. The formulated bulks were gently mixed during the process of adding bulk aluminum phosphate and after completion of final addition thereof, and the pH was checked and then adjusted as necessary. Further, the formulated bulk product was finally stored at 2° C. to 8° C. The manufactured multivalent pneumococcus conjugate vaccine formulations are shown in the following Table.

TABLE 1

| Configurations of Comparative Examples and Experimental Examples | |
| --- | --- |
| Classification | Constitution |
| Comparative Example 1 | PBS |
| Comparative Example 2 | CRM$_{197}$ |
| Comparative Example 3 | Prevena 13 ®Product |
| Comparative Example 4 | Synflorix ®Product |
| Experimental Example 1 | Vaccine compositions in each of which polysaccharides of serotypes 1, 3, 4, 5, 6A, 6B, 7F, 9V, 14, 18C, 19A, 19F, and 23F are conjugated to CRM$_{197}$ carrier protein (Human dose) |
| Experimental Example 2 | Vaccine compositions in each of which polysaccharides of serotypes 1, 3, 4, 5, 6A, 6B, 7F, 9V, 14, 18C, 19A, 19F, and 23F are conjugated to CRM$_{197}$ carrier protein (¼, Human dose) |
| Experimental Example 3 | Vaccine compositions in each of which polysaccharides of serotypes 1, 3, 4, 5, 6A, 6B, 7F, 9V, 14, 18C, 19A, 19F, and 23F are conjugated to CRM$_{197}$ carrier protein (1/16, Human dose) |

(✕· Synflorix is a GSK product, which corresponds to a 11-valent product)

The obtained vaccine composition included 2 μg of each saccharide (4 μg in the case of 6B), about 35 μg of a CRM197 carrier protein, 0.125 mg of an adjuvant of an aluminum element (0.5 mg of aluminum phosphate), about 4.25 mg of sodium chloride, about 295 μg of a succinate buffer solution, and about 100 μg of polysorbate 80 in a total of 0.5 mL thereof.

Example 3-2. ELISA Measurement of Serotype-Specific IgG Concentration

Each of the 13-valent pneumococcal vaccine compositions manufactured in the above Examples was tested as follows in order to confirm whether the compositions have the ability to induce an immune reaction in mice. The corresponding immunogenicity was confirmed by measuring the IgG concentration of serum through antigen-specific ELISA.

Each of the formulated multivalent pneumococcal vaccine compositions and Prevenar 13 ®, which was a control group, was immunized into the muscles of mice (C57BL/6) at the 0th week, 2nd week, and 4th week at planned human clinical doses (the content of each polysaccharide was 4.4 μg/mL, except for the case where 6B was 8.8 μg/mL, which was considered as 100%, and the content of some serotypes was adjusted as needed). Each serum was collected one week after the last inoculation. The serotype-specific IgG concentration was measured using ELISA for each collected serum.

This will be described below in detail. Analysis was performed using the dilution multiple of each serum at which an absorbance value was reduced to less than 0.175. Serotype capsular polysaccharides were applied at a concentration of 5 μg/ml on a 96-well immunoplate and then left at 4° C. In order to block non-specific bonding, the serum that was diluted using 5 μg/ml of cell wall capsular polysaccharides (CWPS) and 22F was added to the coated plate. After 2 hours, treatment with anti-mouse IgG, which was an HRP-attached secondary antibody, was performed, and the resultant plate was left at room temperature for 1 hour. After 1 hour, the substrate that was reacted with HRP (3,3%5,5'-tetramethylbenzkline; TMB) was treated for 10 minutes so as to terminate the reaction using 2N H$_2$SO$_4$, and the absorbance was then measured at 450 nm after 10 minutes.

TABLE 2

| Comparison of IgG relative to 13-valent serotype one week after third immunization | | | |
| --- | --- | --- | --- |
| | PCV13/Prevnar13 ELISA IgG relative comparison | | |
| Serotype | Full dose | ¼ dose | 1/16 dose |
| 1 | + | + | + |
| 3 | + | + | + |
| 4 | + | + | + |
| 5 | + | + | + |
| 6A | + | + | + |
| 6B | + | + | + |
| 7F | + | + | + |
| 9V | + | + | + |
| 14 | + | + | + |
| 18C | + | + | + |
| 19A | + | + | + |
| 19F | + | + | + |
| 23F | + | + | + |

(✕· +: An effect of one to three times that of the control group was confirmed)

Figure 1:
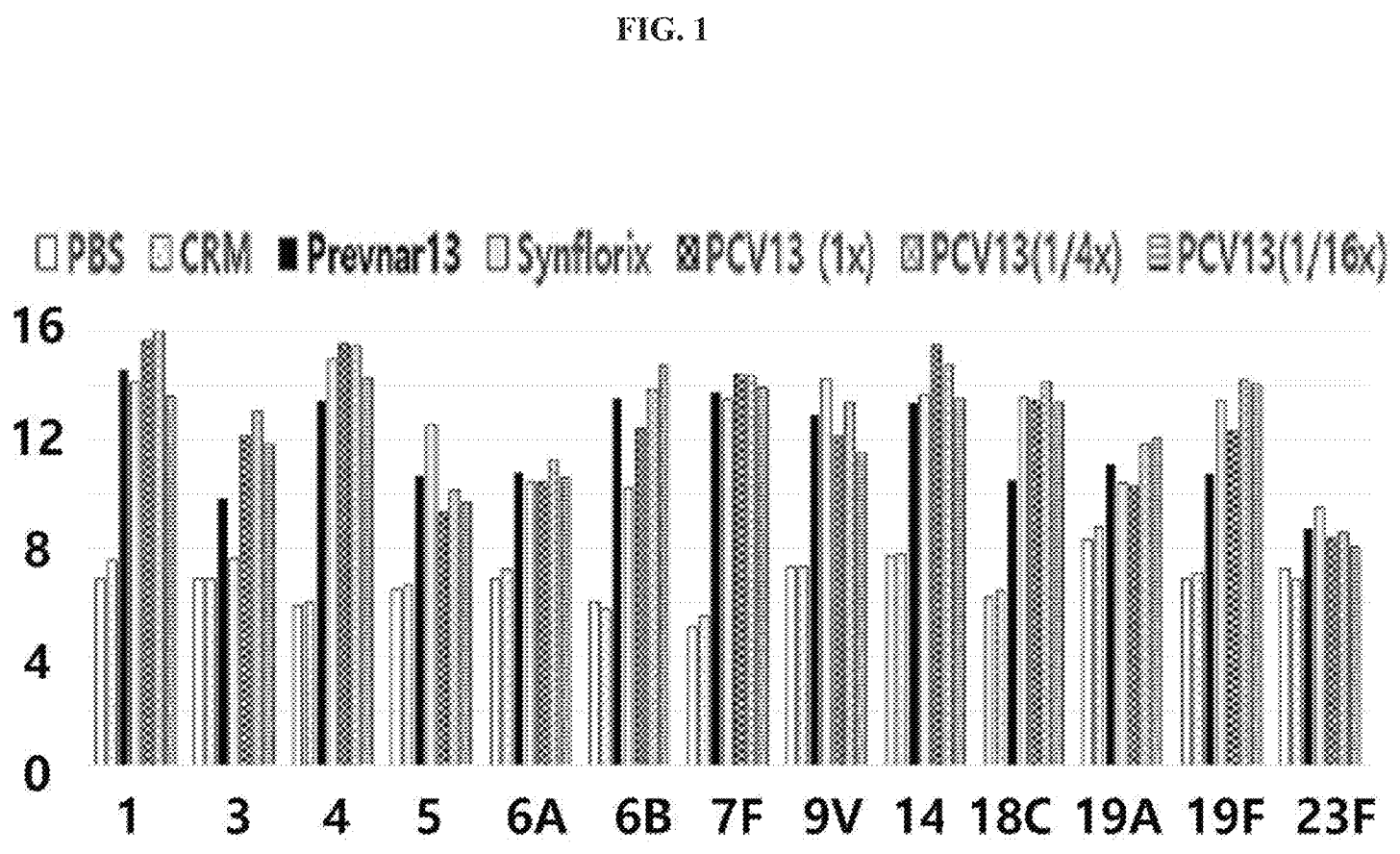

The present inventors compared the effect of the commercially available conventional 13-valent conjugate with that of Prevenar 13 prior to the manufacture of a multivalent mixed vaccine. As a result, the serotypes correlated with the concentration-dependent IgG titer of the 13-valent immunogenic composition and other serotypes that were not correlated therewith were confirmed. Further, in comparison with Prevenar 13, it was confirmed that a similar IgG titer was secured regardless of the concentration. (Table 2 and FIG. 1)

Example 3-3. Opsonin Test of Antibody Function (MOPA Method)

Antibody function was assessed by testing sera through a MOPA assay. A well-known method (a multiplexed opsonophagocytic killing assay (UAB-MOPA) test method for measuring an antibody function against pneumococcus, 2013) was performed as the analysis method, and the experimental method is described in brief below.

A process in which phagocytic cells ingurgitate pathogens through complements and antibodies is called opsonization. In order to confirm the ability of serotype-specific antibodies generated by vaccine inoculation, analysis was performed through a single/multiplex opsonophagocytic assay, which is an experimental method using an opsonization process. One or two or more serotypes of Pneumococcus having different antibiotic resistances, sera, complements, and phagocytic cells were cultivated together, thus inducing the phagocytosis process. Each serotype was smeared on an agar medium to which antibiotics having resistance were added, thus measuring the number of colonies according to the dilution multiple of the serum. In the control group, 50% removal rate (50% morbidity) of strains was measured based on the number of colonies in which 100% of strains survived (0% morbidity), whereby opsonization indexes (OI) were compared using the dilution multiple at which the 50% removal rate of each sample was ensured.

TABLE 3

Comparison of MOPA relative to 13-valent serotype one week after third immunization

| | PCV13/Prevnar13 OPA relative comparison | | |
| Serotype | Full dose | ¼ dose | 1/16 dose |
| --- | --- | --- | --- |
| 1 | +++ | +++ | + |
| 3 | +++ | ++++ | +++ |
| 4 | +++ | +++ | + |
| 5 | + | + | + |
| 6A | + | ++ | + |
| 6B | + | + | + |
| 7F | ++ | ++ | + |
| 9V | + | + | + |
| 14 | +++ | ++ | + |
| 18C | ++ | ++++ | ++++ |
| 19A | + | ++++ | +++ |
| 19F | +++ | ++++ | ++++ |
| 23F | + | + | + |

(※ +: An effect of one to three times that of the control group was confirmed/++: An effect of three to five times that of the control group was confirmed/+++: An effect of five to seven times that of the control group was confirmed/++++: An effect of five to seven times that of the control group was confirmed)

As a result, antibody titers and OPA titers of all serotypes, which were higher than or similar to those of Prevenar 13, were confirmed, and a great immunity interference effect was not confirmed in the 13-valent immunogenic composition. There were some groups exhibiting a low titer at predetermined administration concentrations in predetermined serotypes, but this phenomenon was confirmed to be a phenomenon already well known in experiments and some papers of 7-valent immunogenic composition. In the above ELISA titer analysis, a titer similar to that of Prevenar 13 was confirmed. However, with respect to the titer of OPA, in the case of some serotypes, it was confirmed that serotypes having titers even higher than and similar to that of Prevenar 13 were distributed in different ways. This shows that the reliability/discrimination ability is higher in the OPA result than in the ELISA result (Table 3 and FIG. 2).

Example 4. Formulation and Immunogenic Studies of 19-Valent Pneumococcus Vaccine Example 4-1. Formulation of 19-Valent Pneumococcus Vaccine The following immunogenic compositions were obtained with reference to the above Examples, and the multivalent pneumococcal conjugate vaccine formulation of each constitution is shown in the following Table.

TABLE 4

Configurations of Comparative Examples and Experimental Examples

| Classification | Constitution |
| --- | --- |
| Comparative Example 1 | Prevenar 13 ®Product |
| Experimental Example 1 | Vaccine compositions in each of which polysaccharides of serotypes 1, 3, 4, 5, 6A, 6B, 7F, 9V, 14, 18C, 19A, 19F, and 23F and polysaccharides of serotypes 10A, 11A, 15B, 22F, 23A, and 35B are conjugated to $CRM_{197}$ carrier protein (Human dose) |
| Experimental Example 2 | Vaccine compositions in each of which polysaccharides of serotypes 1, 3, 4, 5, 6A, 6B, 7F, 9V, 14, 18C, 19A, 19F, and 23F and polysaccharides serotypes 10A, 11A, 15B, 22F, 23A, and 35B are conjugated to $CRM_{197}$ carrier protein (¼, Human dose) |
| Experimental Example 3 | Vaccine compositions in each of which polysaccharides of serotypes 1, 3, 4, 5, 6A, 6B, 7F, 9V, 14, 18C, 19A, 19F, and 23F and polysaccharides of serotypes 10A, 11A, 15B, 22F, 23A, and 35B are conjugated to $CRM_{197}$ carrier protein (1/16, Human dose) |

Example 4-2. ELISA Measurement of 19-Valant Serotype-Specific IgG Concentration

ELISA was performed using sera obtained from mice, as in the Example above, and the results are as follows.

TABLE 5

Comparison of IgG relative to 19-valent serotype one week after third immunization

| Serotype | PCV19-Full dose | PCV19-¼ dose | PCV19-1/16 dose |
| --- | --- | --- | --- |
| 1 | + | + | + |
| 3 | + | + | + |
| 4 | + | + | ++ |
| 5 | + | + | + |
| 6A | + | + | + |
| 6B | + | + | + |
| 7F | + | + | + |
| 9V | + | + | + |
| 10A | + | + | + |
| 11A | + | + | + |
| 14 | + | + | + |
| 15B | + | + | + |
| 18C | + | + | + |
| 19A | + | + | + |
| 19F | + | + | + |
| 22F | + | + | + |
| 23A | + | + | + |
| 23F | + | + | + |
| 35B | + | + | + |

(※ +: An effect of one to three times that of the control group was confirmed/++: An effect of three to five times that of the control group was confirmed)

As a result, it was confirmed that the $PCV19\text{-}CRM_{197}$ full dose produced a high serotype-specific IgG concentration for all nineteen serotypes. In the case of $PCV19\text{-}CRM_{197}$, the serotype that was present in common with Prevenar 13 exhibited a serotype-specific IgG concentration equal to or higher than that of Prevenar 13, and the added serotypes 10A, 11A, 15B, and 22F each exhibited a high serotype-specific IgG concentration.

Figure 3:
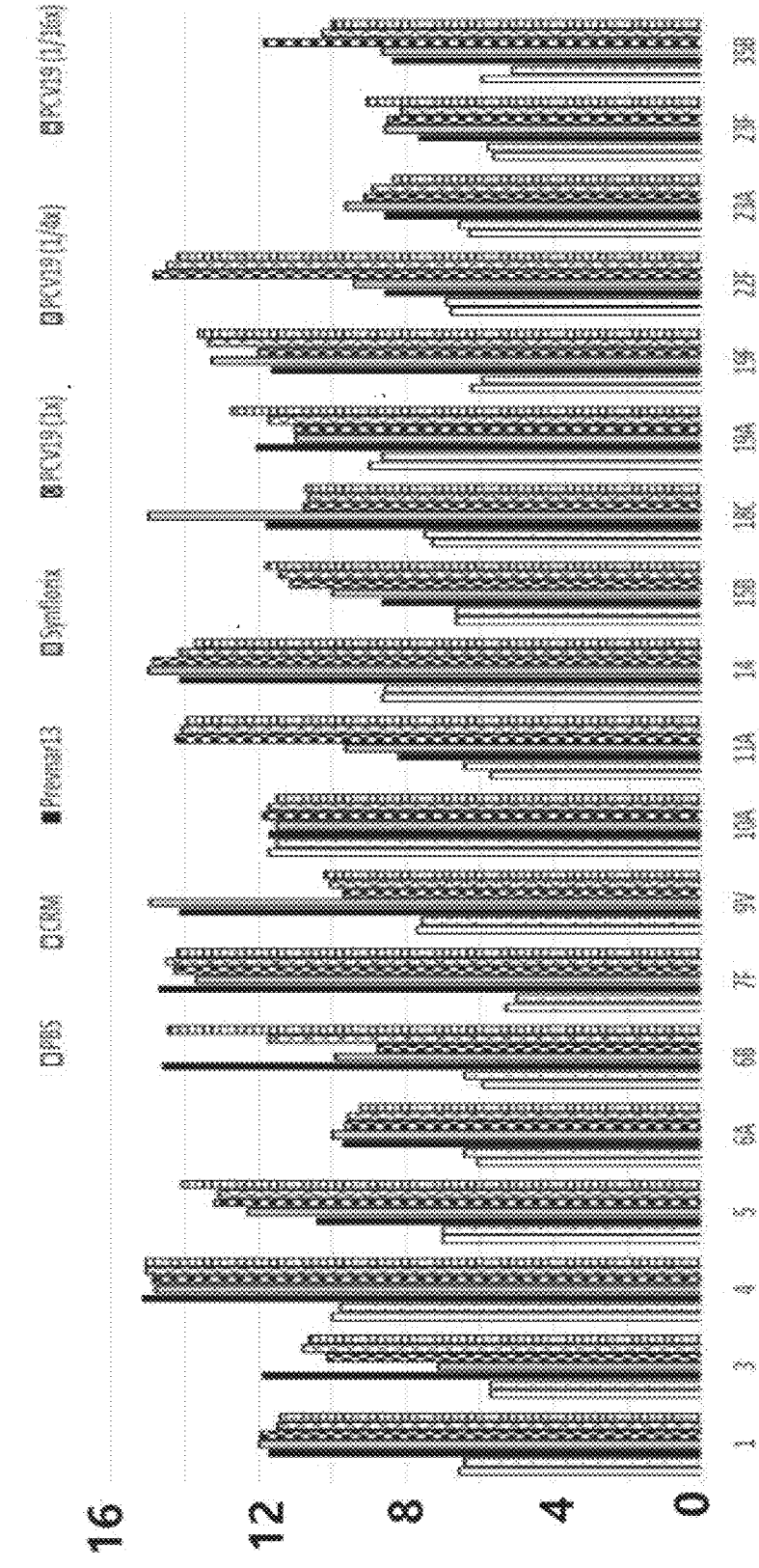
FIG. 3 is a view showing the IgG ELISA result of a 19-valent pneumococcus vaccine serotype.

The serotypes that were present in common with Prevenar 13 exhibited serotype-specific IgG concentrations equal to or higher than those of Prevenar 13, and the added serotypes 10A, 11A, 15B, 22F, 23A, and 35B each exhibited a high serotype-specific IgG concentration (Table 5 and FIG. 3).

Example 4-3. 19-Valent Antibody Opsonophagocytic Assay (MOPA)

OPA analysis was performed using sera obtained from mice with reference to the above Examples, and the results are as follows.

TABLE 6

Comparison of MOPA for 19-valent serotypes
one week after third immunization

| Serotype | PCV19-Full dose | PCV19-¼ dose | PCV19-¹⁄₁₆ dose |
|---|---|---|---|
| 1 | + | + | + |
| 3 | + | + | + |
| 4 | + | + | + |
| 5 | + | + | + |
| 6A | + | + | + |
| 6B | + | + | + |
| 7F | + | + | + |
| 9V | + | + | + |
| 10A | + | + | + |
| 11A | + | + | + |
| 14 | + | + | + |
| 15B | + | + | + |
| 18C | + | + | + |
| 19A | + | + | + |
| 19F | + | + | + |
| 22F | +++ | +++ | + |
| 23A | + | + | + |
| 23F | + | + | + |
| 35B | + | + | + |

(X: An effect of one to three times that of the control group was confirmed/++: An effect of three to five times that of the control group was confirmed/+++: An effect of five to seven times that of the control group was confirmed)

As a result, it was confirmed that all serotypes exhibited functional antibody titers equal to or higher than that of Prevenar 13 in all groups of PCV19-CRM$_{197}$ full, ¼, and ¹⁄₁₆ doses.

It was confirmed that 23A and 35B generated excellent serotype-functional antibodies for almost all serotypes including groups of PCV19 full, ¼, and ¹⁄₁₆ doses. The serotype that was present in common with Prevenar 13 provided a functional antibody equal to or better than that of Prevenar 13, and the added serotypes 10A, 11A, 15B, 22F, 23A, and 35B each provided an excellent functional antibody.

Figure 4:
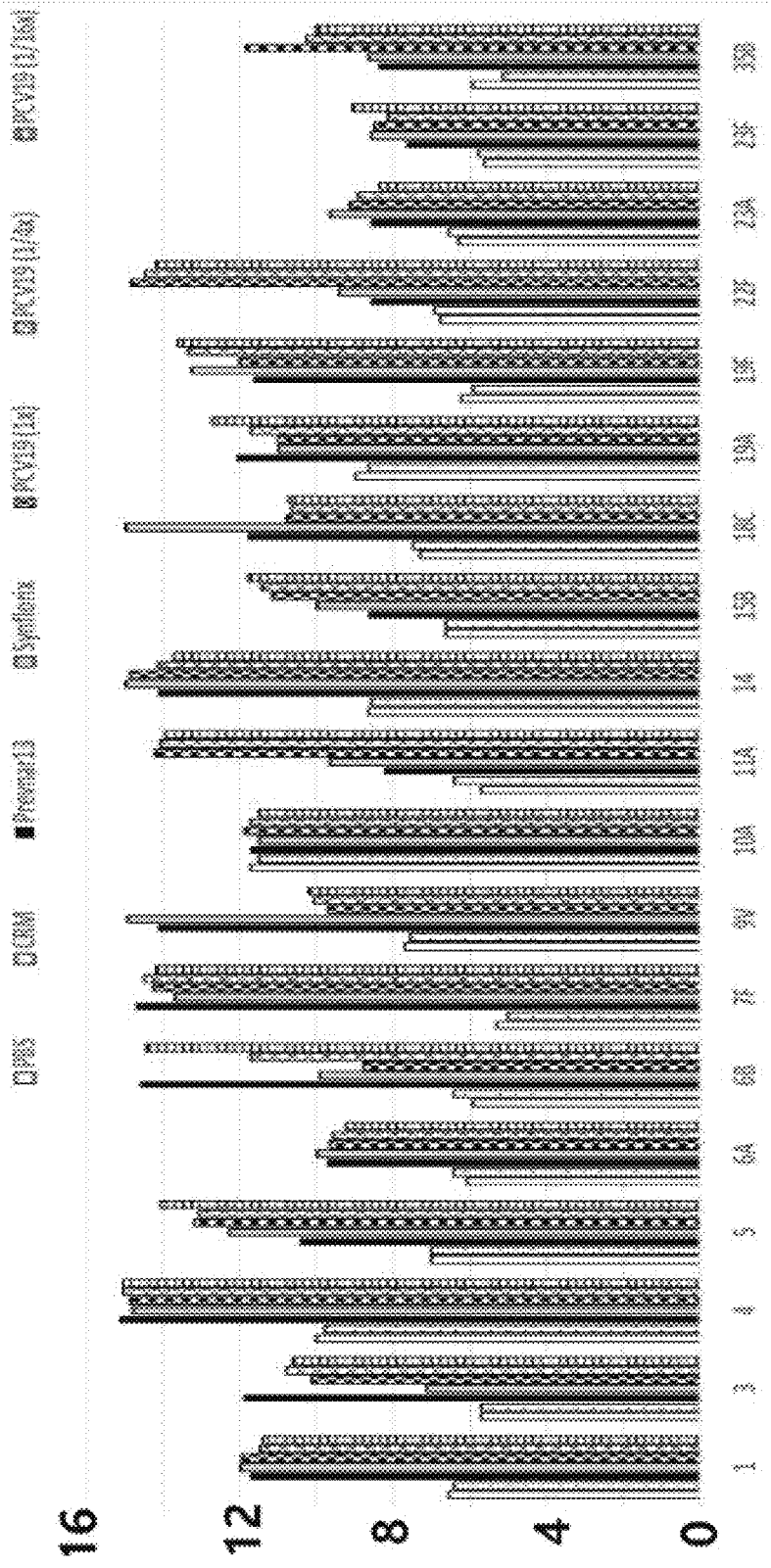
FIG. 4 is a view showing the OPA result of a 19-valent pneumococcus vaccine serotype.

Moreover, in the above results, the PCV19 composition did not show a serotype of immunogenicity inferior to that of PCV13 which is a positive control group. A titer similar to or higher than that of PCV13 was finally confirmed, so the PCV19 composition was again confirmed not to have an immunity interference effect (Table 6 and FIG. 4).

Example 5. Formulation and Immunogenic Studies of 20-Valent Pneumococcus Vaccine

Example 5-1. Formulation of 20-Valent Pneumococcus Vaccine

The following immunogenic compositions were obtained with reference to the above Examples, and the multivalent pneumococcal conjugate vaccine formulation of each constitution is shown in the following Table.

TABLE 7

Configurations of Comparative Examples
and Experimental Examples

| Classification | Constitution |
|---|---|
| Comparative Example 1 | Prevenar 13 ®Product |
| Experimental Example 1 | Vaccine compositions in each of which polysaccharides of serotypes 1, 3, 4, 5, 6A, 6B, 7F, 9V, 14, 18C, 19A, 19F, and 23F and polysaccharides of serotypes 10A, 11A, 12F, 15B, 22F, 23A, and 35B are conjugated to CRM$_{197}$ carrier protein (Human dose) |
| Experimental Example 2 | Vaccine compositions in each of which polysaccharides of serotypes 1, 3, 4, 5, 6A, 6B, 7F, 9V, 14, 18C, 19A, 19F, and 23F and polysaccharides of serotypes 10A, 11A, 12F, 15B, 22F, 23A, and 35B are conjugated to CRM$_{197}$ carrier protein (¼, Human dose) |
| Experimental Example 3 | Vaccine compositions in each of which polysaccharides of serotypes 1, 3, 4, 5, 6A, 6B, 7F, 9V, 14, 18C, 19A, 19F, and 23F and polysaccharides of serotypes 10A, 11A, 12F, 15B, 22F, 23A, and 35B are conjugated to CRM$_{197}$ carrier protein (¹⁄₁₆, Human dose) |

Example 5-2. ELISA Measurement of 20-Valant Serotype-Specific IgG Concentration ELISA was performed using sera obtained from mice, as in the Example above, and the results are as follows.

TABLE 8

Comparison of IgG relative to 20-valent serotype
one week after third immunization

| Serotype | PCV20-Full dose | PCV20-¼ dose | PCV20-¹⁄₁₆ dose |
|---|---|---|---|
| 1 | + | + | + |
| 3 | + | + | + |
| 4 | + | + | + |
| 5 | + | + | + |
| 6A | + | + | + |
| 6B | + | + | + |
| 7F | + | + | + |
| 9V | + | + | + |
| 10A | + | + | + |
| 11A | + | + | + |
| 12F | + | + | + |
| 14 | + | + | + |
| 15B | + | + | + |
| 18C | + | + | + |
| 19A | + | + | + |
| 19F | + | + | + |
| 22F | + | + | + |
| 23A | + | ++ | + |
| 23F | + | + | + |
| 35B | + | + | + |

(X: An effect of one to three times that of the control group was confirmed/++: An effect of three to five times that of the control group was confirmed)

As a result, it was confirmed that the PCV20-CRM$_{197}$ full dose produced a high serotype-specific IgG concentration for all twenty serotypes. In the case of PCV20-CRM$_{197}$, the serotype that was present in common with Prevenar 13 exhibited a serotype-specific IgG concentration equal to or higher than that of Prevenar 13, and the added serotypes 10A, 11A, 15B, and 22F each exhibited a high serotype-specific IgG concentration.

The serotypes that were present in common with Prevenar 13 exhibited serotype-specific IgG concentrations equal to or higher than those of Prevenar 13, and the added serotypes 10A, 11A, 12F, 15B, 22F, 23A, and 35B each exhibited a high serotype-specific IgG concentration (Table 8).

Example 5-3. 20-Valent Antibody Opsonophagocytic Assay (MOPA)

OPA analysis was performed using sera obtained from mice with reference to the above Examples, and the results are as follows.

TABLE 9

Comparison of MOPA for 20-valent serotypes
one week after third immunization

| Serotype | PCV20-Full dose | PCV20-¼ dose | PCV20-¹⁄₁₆ dose |
|---|---|---|---|
| 1 | + | + | + |
| 3 | + | + | + |
| 4 | + | + | + |
| 5 | + | + | + |
| 6A | + | + | + |
| 6B | + | + | + |
| 7F | + | + | + |
| 9V | + | + | + |
| 10A | + | + | + |
| 11A | + | + | + |
| 12F | ++ | ++ | + |
| 14 | + | + | + |
| 15B | + | ++ | ++ |
| 18C | + | + | + |
| 19A | + | + | + |
| 19F | + | + | + |
| 22F | ++ | ++ | ++ |
| 23A | ++ | ++ | + |
| 23F | + | + | + |
| 35B | ++ | + | + |

(X: An effect of one to three times that of the control group was confirmed/++: An effect of three to five times that of the control group was confirmed/+++: An effect of five to seven times that of the control group was confirmed)

As a result, it was confirmed that all serotypes exhibited functional antibody titers equal to or higher than that of Prevenar 13 in all groups of PCV20-CRM$_{197}$ full, ¼, and ¹⁄₁₆ doses.

It was confirmed that serotype-functional antibodies were generated at a good level for all serotypes in PCV20 full-, ¼-, and ¹⁄₁₆-does groups in which seven new serotypes were included. The serotype that was present in common with Prevenar 13 provided a functional antibody equal to or better than that of Prevenar 13, and the added serotypes 10A, 11A, 12F, 15B, 22F, 23A, and 35B each provided an excellent functional antibody.

Moreover, in the above results, the PCV20 composition did not show a serotype of immunogenicity inferior to that of PCV13 which is a positive control group. A titer similar to or higher than that of PCV13 was finally confirmed, so the PCV20 composition was again confirmed not to have an immunity interference effect (Table 9).

The invention claimed is:

1. A multivalent immunogenic composition comprising polysaccharide-protein conjugates, each conjugate comprising *Streptococcus pneumoniae*-derived capsular polysaccharides of different serotypes conjugated to a carrier protein, wherein the capsular polysaccharides include:
thirteen serotypes consisting of serotypes 1, 3, 4, 5, 6A, 6B, 7F, 9V, 14, 18C, 19A, 19F, and 23F, and six serotypes consisting of serotypes 10A, 11A, 15B, 22F, 23A, and 35B, or seven serotypes consisting of serotypes 10A, 11A, 12F, 15B, 22F, 23A, and 35B; and
wherein the serotypes 4, 15B, and 19A are not hydrolyzed.

2. The multivalent immunogenic composition of claim 1, wherein the carrier protein is any one selected from the group consisting of a diphtheria toxoid, a tetanus toxoid, a whooping cough toxoid, a cholera toxoid, an *E. coli*-derived inactivated toxin, a *Pseudomonas aeruginosa*-derived inactivated toxin, and a bacterial outer membrane protein (OMP).

3. The multivalent immunogenic composition of claim 2, wherein the diphtheria toxoid is any one selected from the group consisting of CRM$_{197}$, CRM$_{173}$, CRM$_{228}$, and CRM$_{45}$.

4. A multivalent immunogenic composition comprising polysaccharide-protein conjugates, each conjugate comprising *Streptococcus pneumoniae*-derived capsular polysaccharides of different serotypes conjugated to a carrier protein,
wherein the capsular polysaccharides include
a) capsular polysaccharides are thirteen serotypes consisting of serotypes 1, 3, 4, 5, 6A, 6B, 7F, 9V, 14, 18C, 19A, 19F, and 23F, and
b) capsular polysaccharides of six serotypes consisting of serotypes 10A, 11A, 15B, 22F, 23A, and 35B, or of seven serotypes consisting of serotypes 10A, 11A, 12F, 15B, 22F, 23A, and 35B,
wherein the serotypes 4, 15B, and 19A are not hydrolyzed, and
wherein a method of conjugating the capsular polysaccharides to the carrier protein is one or more methods selected from the group consisting of a CDAP conjugation method, a reductive amination method, and a thiol-malemide method.

5. The multivalent immunogenic composition of claim 1, further comprising: an adjuvant.

6. The multivalent immunogenic composition of claim 5, wherein the adjuvant is an aluminum salt.

7. The multivalent immunogenic composition of claim 6, wherein the aluminum salt is any one selected from the group consisting of aluminum phosphate, aluminum sulfate, and aluminum hydroxide.

8. The multivalent immunogenic composition of claim 1, wherein the multivalent immunogenic composition includes polysaccharide in an amount of 0.1 to 100 μg.

9. A method of inducing an immune reaction against a *Streptococcus pneumoniae*-capsular polysaccharide conjugate, comprising:
administering the multivalent immunogenic composition according to claim 1 in a prophylactically or therapeutically effective amount.

10. A method of preventing or treating pneumococcus-related diseases, comprising:
administering the multivalent immunogenic composition according to claim 1 in a prophylactically or therapeutically effective amount.

\* \* \* \* \*